(12) United States Patent
Yokoyama et al.

(10) Patent No.: US 10,374,544 B2
(45) Date of Patent: Aug. 6, 2019

(54) METHOD FOR ESTIMATING SERVICE LIFE OF MOTOR, MOTOR CONTROL SYSTEM, BLOWER SYSTEM, AND MULTICOPTER SYSTEM

(71) Applicant: Nidec Corporation, Kyoto (JP)

(72) Inventors: Yuichiro Yokoyama, Kyoto (JP); Shoki Yamazaki, Kyoto (JP); Junya Matsuyama, Kyoto (JP)

(73) Assignee: NIDEC CORPORATION, Kyoto (JP)

( * ) Notice: Subject to any disclaimer, the term of this patent is extended or adjusted under 35 U.S.C. 154(b) by 0 days.

(21) Appl. No.: 15/841,354

(22) Filed: Dec. 14, 2017

(65) Prior Publication Data

US 2018/0183379 A1 Jun. 28, 2018

(30) Foreign Application Priority Data

Dec. 27, 2016 (JP) .................. 2016-253478

(51) Int. Cl.
*H02P 5/68* (2006.01)
*B60L 11/14* (2006.01)
(Continued)

(52) U.S. Cl.
CPC ................ *H02P 29/60* (2016.02); *G01K 3/10* (2013.01); *G01N 25/00* (2013.01); *H02P 5/00* (2013.01); *H02P 27/08* (2013.01); *H02P 29/40* (2016.02)

(58) Field of Classification Search
CPC ................ H02H 7/08; H02P 6/15; H02P 7/29
See application file for complete search history.

(56) References Cited

U.S. PATENT DOCUMENTS 8,498,826 B2 * 7/2013 Nagathil ............ G05B 19/4065
318/490
2006/0142901 A1 6/2006 Frankel et al.
(Continued)

FOREIGN PATENT DOCUMENTS

CN 102080648 B 7/2014
JP 11-175169 A 7/1999
(Continued)

*Primary Examiner* — Bickey Dhakal
*Assistant Examiner* — Charles S Laughlin
(74) *Attorney, Agent, or Firm* — Keating & Bennett, LLP

(57) ABSTRACT

A method for estimating a service life of a motor that is driven by variable duty cycle control. The method includes calculating an elapsed service life ratio representing a ratio of an elapsed service life to all service life according to the following formula to estimate the service life of the motor:

$$L_s = \sum_i \left(\frac{t_i}{L_i \times (1.5)^m}\right) \quad m = \frac{40 - \max(40, K_i)}{10},$$

where $L_s$ represents the elapsed service life ratio, $t_i$ represents a driving time in a section i, $L_i$ represents a service life expectancy at a duty cycle $D_i$ in the section i and at an environmental temperature of the motor being 40° C., and $K_i$ represents a temperature in the section i.

10 Claims, 10 Drawing Sheets

(51) Int. Cl.
*H02P 29/60* (2016.01)
*G01N 25/00* (2006.01)
*H02P 29/40* (2016.01)
*H02P 5/00* (2016.01)
*G01K 3/10* (2006.01)
*H02P 27/08* (2006.01)

(56) References Cited

U.S. PATENT DOCUMENTS

2008/0048603 A1* 2/2008 Discenzo ............ G05B 19/4063
318/561
2015/0051846 A1 2/2015 Masuya
2016/0065113 A1* 3/2016 Gauthier ................. H02P 6/182
318/490
2016/0368346 A1* 12/2016 Nishikawa ......... B60H 1/00457

FOREIGN PATENT DOCUMENTS

| JP | 2012-87720 A | 5/2012 |
| JP | 2014-153350 A | 8/2014 |
| JP | 2016-71011 A | 5/2016 |

* cited by examiner

| Duty[%] | Life[h] | ⊿t[℃] |
|---|---|---|
| 100 | 80000 | 42.4 |
| 90 | 142000 | 28.2 |
| 80 | 197000 | 20.2 |
| 70 | 251000 | 14.2 |
| 60 | 298000 | 10 |
| 50 | 331000 | 7.4 |
| 40 | 356000 | 5.6 |
| 30 | 372000 | 4.5 |

Fig.2

METHOD FOR ESTIMATING SERVICE LIFE OF MOTOR, MOTOR CONTROL SYSTEM, BLOWER SYSTEM, AND MULTICOPTER SYSTEM

CROSS REFERENCE TO RELATED APPLICATIONS

This application claims the benefit of priority to Japanese Patent Application No. 2016-253478 filed on Dec. 27, 2016. The entire contents of this application are hereby incorporated herein by reference.

BACKGROUND OF THE INVENTION

1. Field of the Invention

The present disclosure relates to a method for estimating a service life of a motor.

2. Description of the Related Art

In the related art, motors have been installed in a variety of apparatuses, and each motor has its service life. For example, Japanese Unexamined Patent Application Publication No. 2016-71011 discloses an image forming apparatus in which a cooling fan including a fan motor is installed.

The image forming apparatus according to the above Japanese Unexamined Patent Application Publication No. 2016-71011 estimates the service life of the cooling fan by the following method. A central processing unit (CPU) included in the image forming apparatus calculates the temperature of the cooling fan on the basis of an outside air temperature detected by a temperature sensor and a temperature increase value in each operation mode. Then, on the basis of the calculated temperature of the cooling fan and according to a correction formula, the CPU corrects the driving time of the cooling fan. Then, the CPU calculates the total driving time from the corrected driving time and determines whether the calculated total driving time exceeds an estimated service-life limit.

However, a variety of motors such as fan motors are often used in a condition in which the rotational speeds are changed. The service life estimating method according to the above Japanese Unexamined Patent Application Publication No. 2016-71011 calculates the total driving time only on the basis of the temperature of the cooling fan and does not take into account the rotational speed of a fan motor. Therefore, it is not possible to estimate the service life of a motor with high accuracy in a use condition in which the rotational speed thereof is changed.

SUMMARY OF THE INVENTION

An exemplary method for estimating a service life of a motor according to an aspect of the present disclosure is a method for estimating a service life of a motor that is driven by variable duty cycle control, the method including calculating an elapsed service life ratio representing a ratio of an elapsed service life to all service life according to the following formula to estimate the service life of the motor:

$$L_s = \sum_i \left( \frac{t_i}{L_i \times (1.5)^m} \right) \quad m = \frac{40 - \max(40, K_i)}{10},$$

where $L_s$ represents the elapsed service life ratio, $t_i$ represents a driving time in a section i, $L_i$ represents a service life expectancy at a duty cycle $D_i$ in the section i and at an environmental temperature of the motor being 40° C., and $K_i$ represents a temperature in the section i.

An exemplary motor control system according to an aspect of the present disclosure includes a motor that is driven by variable duty cycle control, and a control unit that reads driving information of the motor. The control unit includes a calculation unit that calculates an elapsed service life ratio representing a ratio of an elapsed service life to all service life of the motor according to the following formula:

$$L_s = \sum_i \left( \frac{t_i}{L_i \times (1.5)^m} \right) \quad m = \frac{40 - \max(40, K_i)}{10},$$

where $L_s$ represents the elapsed service life ratio, $t_i$ represents a driving time in a section i, $L_i$ represents a service life expectancy at a duty cycle $D_i$ in the section i and at an environmental temperature of the motor being 40° C., and $K_i$ represents a temperature in the section i.

An exemplary blower system according to an aspect of the present disclosure includes the motor control system having the above configuration, and a blower including the motor and an impeller that is fixed on a rotation unit of the motor and that includes a plurality of blades.

An exemplary method for estimating a service life of a motor according to an aspect of the present disclosure is a method for estimating a service life of a motor that is driven by variable duty cycle control, the method including calculating an elapsed service life ratio representing a ratio of an elapsed service life to all service life according to the following formula to estimate the service life of the motor:

$$L_s = \sum_i \left( \frac{t_i}{L_i \times (1.5)^m} \right) \quad m = \frac{(40 + \Delta t) - \max(40 + \Delta t, K_i)}{10},$$

where $L_s$ represents the elapsed service life ratio, $t_i$ represents a driving time in a section i, $L_i$ represents a service life expectancy at a duty cycle $D_i$ in the section i and at an environmental temperature of the motor being 40° C., $K_i$ represents a temperature of the motor in the section i, and $\Delta t$ represents a temperature increase value of the motor at the duty cycle $D_i$ in the section i and at the environmental temperature of the motor being 40° C.

An exemplary motor control system according to an aspect of the present disclosure includes a motor that is driven by variable duty cycle control, and a control unit that reads driving information of the motor. The control unit includes a calculation unit that calculates an elapsed service life ratio representing a ratio of an elapsed service life to all service life of the motor according to the following formula:

$$L_s = \sum_i \left( \frac{t_i}{L_i \times (1.5)^m} \right) \quad m = \frac{(40 + \Delta t) - \max(40 + \Delta t, K_i)}{10},$$

where $L_s$ represents the elapsed service life ratio, $t_i$ represents a driving time in a section i, $L_i$ represents a service life expectancy at a duty cycle $D_i$ in the section i and at an environmental temperature of the motor being 40° C., $K_i$ represents a temperature of the motor in the section i, and $\Delta t$ represents a temperature increase value of the motor at the duty cycle $D_i$ in the section i and at the environmental temperature of the motor being 40° C.

An exemplary multi-copter system according to an aspect of the present disclosure includes the motor control system having the above configuration, and a multi-copter main body including the motor and a propeller that is rotatable by the motor.

According to the exemplary method for estimating a service life of a motor, motor control system, blower system, and multi-copter system according to aspects of the present disclosure, it is possible to accurately estimate the service life of the motor in a use condition in which the rotational speed thereof is changed.

The above and other elements, features, steps, characteristics and advantages of the present disclosure will become more apparent from the following detailed description of the preferred embodiments with reference to the attached drawings.

BRIEF DESCRIPTION OF THE DRAWINGS

FIG. 2 is a table illustrating an example of the relationship between a duty cycle, a service life expectancy of a motor, and a temperature increase value of the motor at an environmental temperature of 40° C.

DETAILED DESCRIPTION OF THE PREFERRED EMBODIMENTS

Now, exemplary embodiments of the present disclosure will be described below with reference to the drawings.

Embodiments related to an example in which the present disclosure is applied to a blower system will be described below.

Figure 1:
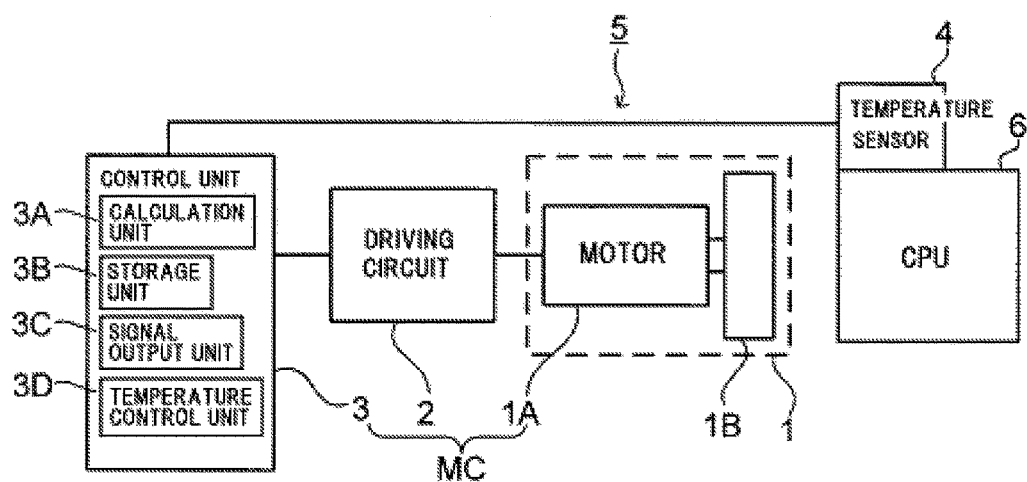
FIG. 1 is a block diagram illustrating a schematic configuration of a blower system according to a first embodiment of the present disclosure.

FIG. 1 is a block diagram illustrating a schematic configuration of a blower system 5 according to a first embodiment of the present disclosure. The blower system 5 illustrated in FIG. 1 includes a blower 1, a driving circuit 2, a control unit 3, and a temperature sensor 4. The blower system 5 cools a CPU 6, which is a heat source as an example of an external apparatus. The blower system 5 and the CPU 6 are included in a personal computer (PC), for example.

The blower 1 includes a motor 1A and an impeller 1B. The motor 1A is configured by a brushless direct current (DC) motor. The motor 1A is, for example, a three-phase motor (U phase, V phase, W phase). The motor 1A includes a stator and a rotor (none of which are illustrated). The stator includes a coil that is wound around a stator core. When current flows in the coil, a magnetic field is generated, and thereby the rotor relatively rotates with respect to the stator. That is, the rotor serves as a rotation unit.

The impeller 1B is fixed on a shaft included in the rotor of the motor 1A. The rotor rotates around the rotational axis of the motor 1A, and thereby the impeller 1B rotates around the rotational axis. The impeller 1B is, for example, a molded item obtained by molding a resin and includes a plurality of blades arranged in the circumferential direction around the rotational axis. By rotating, the impeller 1B generates an air flow in the axial-flow direction, for example. In this case, the CPU 6, which is a cooling target, is disposed in the downstream side of the axial-flow direction of the impeller 1B.

The driving circuit 2 includes a pulse-width modulation (PWM) signal generating unit and a driver (none of which are illustrated). The PWM signal generating unit generates a PWM signal in which the duty cycle is adjusted in such a manner that the rotational speed of the motor 1A corresponds to a target speed that is input from the control unit 3, and outputs the PWM signal to the driver. The driver causes current to flow into the coil of the motor 1A on the basis of the PWM signal, thereby rotatably driving the motor 1A. That is, by variable duty cycle control, the driving circuit 2 changes the rotational speed of the motor 1A.

In the blower system 5, a motor control system MC is configured by the motor 1A, the driving circuit 2, and the control unit 3. That is, the blower system 5 includes the motor control system MC. The control unit 3 includes a calculation unit 3A, a storage unit 3B, a signal output unit 3C, and a temperature control unit 3D.

The temperature sensor 4 is a sensor that detects the temperature of the CPU 6. The temperature control unit 3D generates the target speed in such a manner that the detection temperature detected by the temperature sensor 4 corresponds to a target temperature, and outputs the target speed to the driving circuit 2. Specifically, if the detection temperature becomes higher than the target temperature, the temperature control unit 3D increases the target speed to increase the rotational speed of the motor 1A. If the detection temperature becomes lower than the target temperature, the temperature control unit 3D decreases the target speed to decrease the rotational speed of the motor 1A. Thus, cooling control is performed on the CPU 6, and the temperature of the CPU 6 is controlled to be constant.

The calculation unit 3A, the storage unit 3B, and the signal output unit 3C are components related to the estimation of the service life of the motor 1A, which will be described later in detail.

Next, the estimation of the service life of the motor 1A by using the motor control system MC will be described. On the basis of the duty cycle (driving information) read from the driving circuit 2 and the detection temperature detected by the temperature sensor 4, the calculation unit 3A of the control unit 3 calculates an elapsed service life ratio according to the following Formula (1):

$$L_s = \sum_i \left(\frac{t_i}{L_i \times (1.5)^m}\right) \quad m = \frac{40 - \max(40, K_i)}{10},$$

where $L_s$ represents the elapsed service life ratio, $t_i$ represents a driving time in a section i (driving time of motor), $L_i$ represents a service life expectancy at a duty cycle $D_i$ in the section i and at an environmental temperature of the motor being 40° C., and $K_i$ represents a temperature in the section i.

The elapsed service life ratio represents a ratio of an elapsed service life to all the service life where the service life of the motor 1A is 1. That is, the remaining service life of the motor 1A is $(1-L_s)$. The section i is a temporal section for calculation. The elapsed service life ratio in the section i, which is the value in the brackets on the right side of the above Formula (1), is calculated for each section i by using $t_i$, $L_i$, and $K_i$, and is integrated in the section i, and thereby the elapsed service life ratio $L_s$ is calculated. The duty cycle read from the driving circuit 2 is used as the duty cycle $D_i$, and the detection temperature detected by the temperature sensor 4 is used as the temperature $K_i$.

Now, $L_i$ in the above Formula (1) will be described. In the table illustrated in FIG. 2, Δt [° C.] represents a temperature increase value of a motor obtained when the motor is operated at each duty cycle under the condition in which the environmental temperature of the motor is 40° C. For example, when the duty cycle is 100%, the motor temperature is increased by 42.4° C. from when the motor is not operated, and when the duty cycle is 40%, the motor temperature is increased by 5.6° C. from when the motor is not operated. As the duty cycle increases, the temperature increase value of the motor increases. This is because, as the duty cycle increases, the amount of current flowing in the coil of the motor increases, and the increase value in the coil temperature of the coil increases.

In FIG. 2, if the motor is operated at a duty cycle of 100%, a temperature increase value Δt of the motor is 42.4° C., and a service life expectancy (Life) of the motor in this case is 80000 hours. If the service life expectancy at a duty cycle of 100% is known to be 80000 hours and if the temperature increase value Δt corresponding to each duty cycle is known, the service life expectancy corresponding to each duty cycle is calculated according to the following Formula (2):

Life=A×(1.5)$^B$ B=(C−D)/10 (2), where Life represents the service life expectancy, A represents 80000 (service life expectancy at duty cycle of 100%), C represents 42.4 (temperature increase value Δt at duty cycle of 100%), and D represents a temperature increase value Δt corresponding to a duty cycle for calculation.

Figure 3:
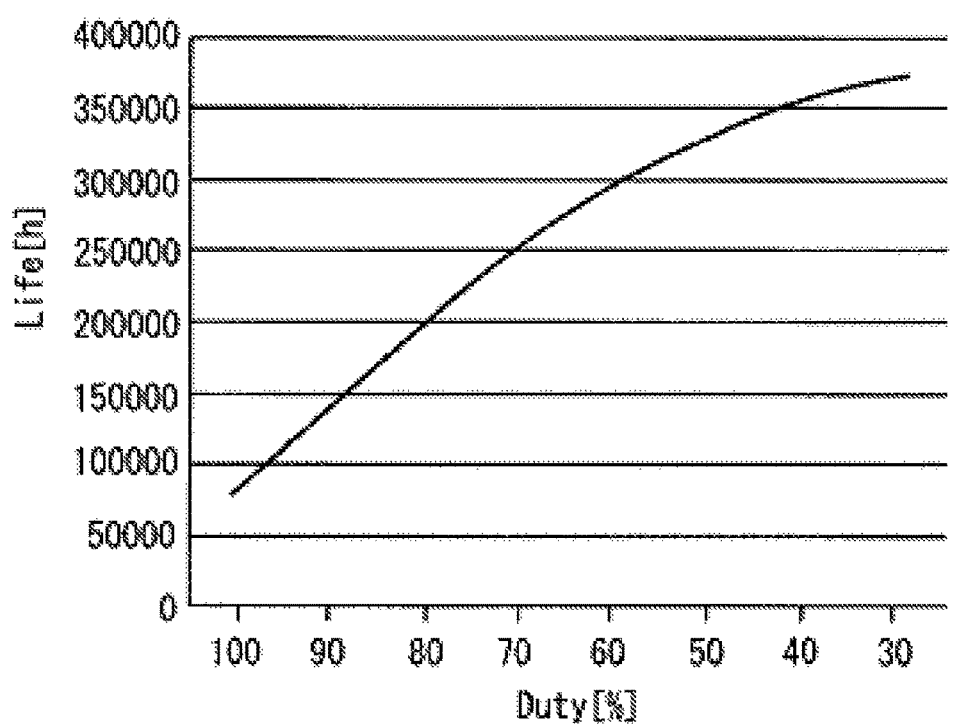
FIG. 3 is a graph illustrating the relationship between the duty cycle and the service life expectancy corresponding to FIG. 2.

The value 1.5 in the above Formula (2) represents 1.5 times/10° C., which is a temperature acceleration factor of the motor. The temperature acceleration factor is defined in the IPC standard IPC-9591. For example, if the duty cycle is 40%, since the corresponding temperature increase value Δt is 5.6, D=5.6 is set, and the service life expectancy Life is calculated as 356000 hours according to the above Formula (2). Thus, by using the above Formula (2), as illustrated in FIG. 2, the life expectancies Life corresponding to the respective duty cycles 90% to 30% are calculated. The relationship between the duty cycle and the service life expectancy illustrated in FIG. 2 is illustrated in FIG. 3 as a graph. As illustrated in FIG. 3, as the duty cycle decreases, the service life expectancy increases.

Note that the specific values of the service life expectancy Life and the temperature increase value Δt illustrated in FIG. 2 are exemplary ones and are changed depending on the specification of the motor.

The value $(1.5)^m$ on the right side of the above Formula (1) represents 1.5 times/10° C., which is a temperature acceleration factor. Here, for example, if the duty cycle $D_i$ and the temperature $K_i$ in the section i are respectively 50% and 50° C., the denominator in the brackets on the right side of the above Formula (1) is calculated as $L_i \times (1.5)^m = 331000 \times (1.5)^{-1}$.

In the motor control system MC according to this embodiment, variable duty cycle control is performed to change the rotational speed of the motor 1A in order to control the temperature of the CPU 6. In the situation in which the rotational speed of the motor 1A is changed in the above manner, by using the above Formula (1), the elapsed service life ratio can be calculated by taking the duty cycle and the temperature into account. Thus, the service life of the motor 1A can be accurately estimated. Note that since the detection value detected by the temperature sensor 4 is used as the temperature $K_i$ in the above Formula (1) in this embodiment, the temperature sensor 4 can be used for both the estimation of the service life and the cooling control.

Figure 4:
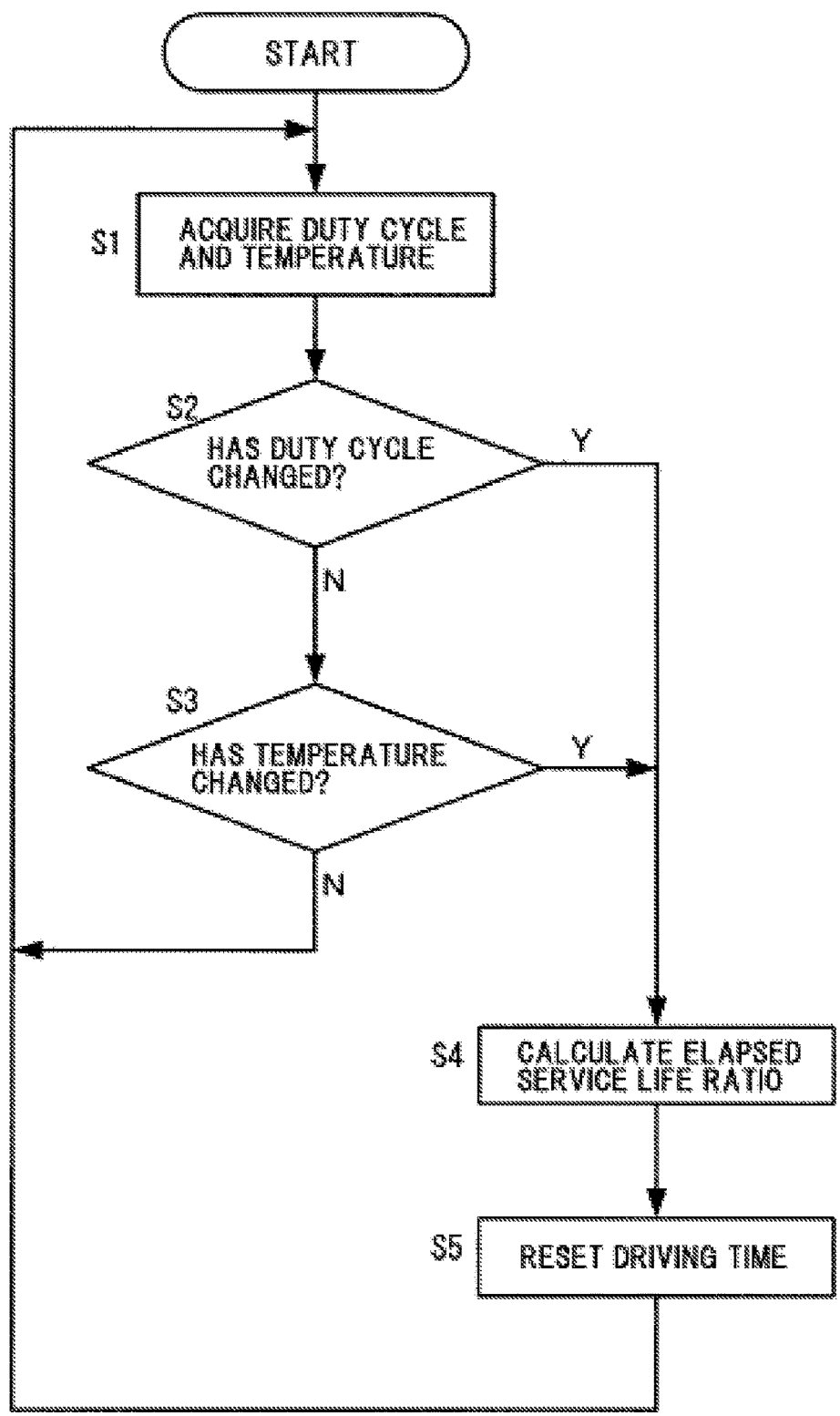
FIG. 4 is a flowchart illustrating an example of a process for calculating an elapsed service life ratio according to the first embodiment of the present disclosure.

FIG. 4 is a flowchart illustrating an example of a process for calculating the elapsed service life ratio according to the above Formula (1). At the start of the flowchart in FIG. 4, the control unit 3 starts to count the driving time of the motor 1A. First, in step S1, the control unit 3 reads information about the duty cycle from the driving circuit 2 and acquires information about the temperature detected by the temperature sensor 4.

In step S2, the control unit 3 determines whether the acquired duty cycle has changed from a last-time duty cycle. If the duty cycle has not changed (N in step S2), the process proceeds to step S3. In step S3, the control unit 3 determines whether the acquired temperature has changed from a last-time temperature. If the temperature has not changed (N in step S3), the process returns to step S1, and the control unit 3 newly acquires the duty cycle and the temperature.

If the duty cycle and the temperature have not changed, steps S1 to S3 are repeated, and the driving time is kept counted. If the duty cycle has changed (Y in step S2), or if the temperature has changed (Y in step S3), the process proceeds to step S4. When the process proceeds to step S4, a section i is defined.

In step S4, on the basis of the last-time duty cycle and temperature acquired in step S1 and the currently counted driving time, the calculation unit 3A calculates the elapsed service life ratio in the section i, which is the value in the brackets on the right side of the above Formula (1). The last-time duty cycle and the temperature are values that have not changed yet.

At this time, the relationship between the duty cycle and the service life expectancy illustrated in FIG. 2, for example, is stored as a table in advance in the storage unit 3B, and the calculation unit 3A determines $L_i$ by referring to the table. Note that the driving circuit 2 may adjust the duty cycle for every 10% as in FIG. 2 or for a smaller value. If the driving circuit 2 adjusts the duty cycle for a small value, values in the table may be interpolated to determine the service life expectancy.

Then, the calculation unit 3A adds the calculated elapsed service life ratio in the section i to the elapsed service life ratio $L_s$ that has been calculated and stored in the storage unit 3B, thereby newly calculating the elapsed service life ratio $L_s$. The calculation unit 3A causes the newly calculated elapsed service life ratio $L_s$ to be stored in the storage unit 3B. That is, by integrating the elapsed service life ratio in the section i, the elapsed service life ratio $L_s$ is calculated. In other words, by integrating the elapsed service life ratio, the total elapsed service life ratio of the motor 1A can be calculated.

After step S4, in step S5, the control unit 3 resets the driving time and starts to count the driving time again. Then, the process returns to step S1.

That is, in the process illustrated in FIG. 4, while the duty cycle changes in cooperation with the temperature, at least one of the temperature and the duty cycle changes. Thus, each time at least one of the temperature and the duty cycle changes, the process proceeds to step S4 in which the elapsed service life ratio is calculated. If the temperature and the duty cycle are stabilized, the process does not proceed to step S4. Accordingly, only the counting of the driving time is continued, and if the temperature changes again, the process proceeds to step S4.

In the process illustrated in FIG. 4, since each section i is defined at the time the duty cycle or the temperature changes, the length of the section i is not constant. However, as another embodiment other than the process illustrated in FIG. 4, for example, the duty cycle and the temperature may be acquired for each fixed unit time to calculate the elapsed service life ratio, in which case the length of the section i is constant. Although the elapsed service life ratio is calculated in synchronization with the driving state of the motor 1A in this embodiment, the method for estimating a service life of a motor is not limited to this embodiment. For example, before the motor is driven, the rotational speed and the temperature of the motor may be assumed in advance, and a predicted elapsed service life ratio may be calculated according to the above formula. The predicted elapsed service life ratio is calculated so as to calculate the remaining service life of the motor, and accordingly, the motor may be replaced or repaired, for example.

If the elapsed service life ratio calculated in the above manner becomes higher than or equal to 1, the service life of the motor ends. Accordingly, in this embodiment, if the elapsed service life ratio calculated by the calculation unit 3A becomes higher than or equal to a set value that is smaller than 1 (e.g., 0.9), the signal output unit 3C of the control unit 3 outputs an alarm signal. The alarm signal is output so that a user can be informed of an alarm by using, for example, a display unit or an audio output unit of a PC in which the blower system 5 and the CPU 6 are provided. Thus, the user can be informed that the remaining service life of the motor is low.

Figure 5:
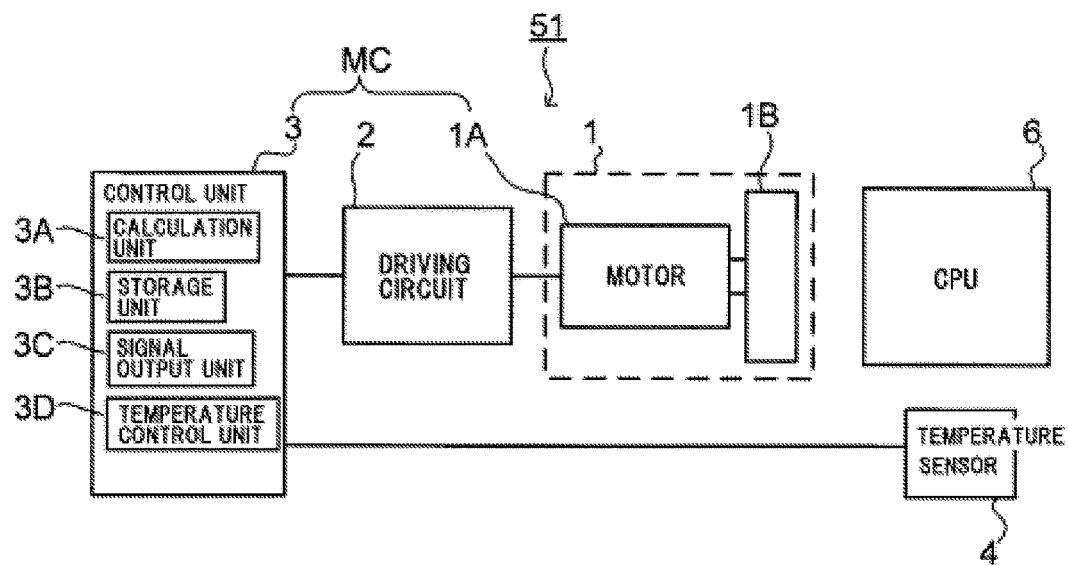
FIG. 5 is a block diagram illustrating a schematic configuration of a blower system according to a first modification of the first embodiment of the present disclosure.

In the above-described blower system 5, the temperature sensor 4 is disposed at a position for detecting the temperature of the CPU 6, which is a heat source. However, the present disclosure is not limited to this example. For example, as in a blower system 51 according to a first modification illustrated in FIG. 5, the temperature sensor 4 may be disposed at a position for detecting the ambient temperature of the CPU 6. In this case, on the basis of the ambient temperature of the CPU 6 detected by the temperature sensor 4, the temperature control unit 3D of the control unit 3 performs variable duty cycle control to control the rotational speed of the motor 1A and to perform cooling control on the CPU 6. In addition, the calculation unit 3A calculates the elapsed service life ratio by using the temperature detected by the temperature sensor 4 as the temperature $K_i$ in the above Formula (1). The temperature sensor 4 may also be used for both cooling control and the estimation of the service life in the above manner.

Figure 6:
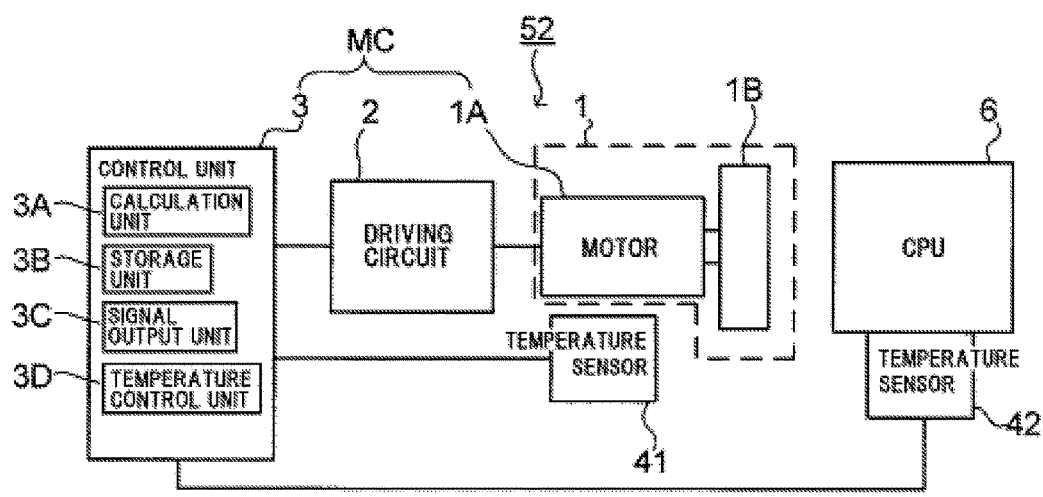
FIG. 6 is a block diagram illustrating a schematic configuration of a blower system according to a second modification of the first embodiment of the present disclosure.

In addition, as an embodiment according to a second modification, a configuration as in a blower system 52 illustrated in FIG. 6 may be employed. The blower system 52 is provided with a temperature sensor 41 that detects the environmental temperature of the motor 1A and a temperature sensor 42 that detects the temperature of the CPU 6, which is a heat source. On the basis of the temperature detected by the temperature sensor 42, the temperature control unit 3D performs variable duty cycle control to control the rotational speed of the motor 1A and to perform cooling control on the CPU 6. In addition, the calculation unit 3A calculates the elapsed service life ratio by using the temperature detected by the temperature sensor 41 as the temperature $K_i$ in the above Formula (1). The use of the environmental temperature of the motor 1A as the temperature $K_i$ enables more accurate estimation of the service life.

In the above-described embodiment, the external apparatus that is the cooling target of the blower is a CPU. Alternatively, the external apparatus may be, for example, an uninterruptible power supply (UPS). In this case, the blower system is provided inside the UPS, and the temperature sensor detects the internal temperature of the UPS.

On the basis of the temperature detected by the temperature sensor, the temperature control unit of the control unit performs variable duty cycle control to control the rotational speed of the motor and to perform cooling control inside the UPS. Thus, even in the situation of heat generation inside the UPS changes in accordance with the situation of a load to the UPS, the internal temperature of the UPS can be controlled.

In addition, the calculation unit calculates the elapsed service life ratio by using the temperature detected by the temperature sensor as the temperature $K_i$ in the above Formula (1). Thus, even in a situation in which the rotational speed of the motor is changed by the cooling control, the service life of the motor can be accurately estimated.

In particular, the UPS is often used for infrastructure equipment such as in a bank, airport, and subway, and therefore, the equipment is not allowed to be completely stopped. Thus, a high reliability is expected for the UPS, and accordingly, a motor used for the UPS has been replaced every three years or so in many cases. However, the replacement period of three years is not based on any reason, and the replacement has been inefficient.

Accordingly, if the service life of the motor used for the UPS can be accurately estimated as in this embodiment, when the calculated elapsed service life ratio becomes higher than or equal to the set value that is smaller than 1, the signal output unit can output an alarm signal. Thus, it is possible to inform a user of the UPS that the remaining service life of the motor is low to encourage the user to replace the motor. Accordingly, the motor can be replaced efficiently.

In addition, the blower system may be provided in a server apparatus. In many cases, a server apparatus is particularly designed to include a plurality of blowers by taking redundancy into account. The redundancy herein is a concept in which motors of the plurality of blowers are driven at a low or middle rotational speed in a normal state, and if malfunction occurs in one of the motors, cooling is recovered by using the remaining motors. In this case, the remaining motors are driven at a higher rotational speed than in a normal state. Thus, the present disclosure is also applied to a server apparatus in which the rotational speeds of motors are changed, and accordingly, the service life of each of the motors can be accurately estimated.

A method for estimating a service life of a motor according to the first embodiment described above is a method for estimating a service life of a motor (1A) that is driven by variable duty cycle control, the method including calculating an elapsed service life ratio representing a ratio of an elapsed service life to all service life according to the following formula to estimate the service life of the motor (1A):

$$L_s = \sum_i \left(\frac{t_i}{L_i \times (1.5)^m}\right) \quad m = \frac{40 - \max(40, K_i)}{10},$$

where $L_s$ represents the elapsed service life ratio, $t_i$ represents a driving time in a section i, $L_i$ represents a service life expectancy at a duty cycle $D_i$ in the section i and at an environmental temperature of the motor being 40° C., and $K_i$ represents a temperature in the section i.

With the above configuration, it is possible to accurately estimate the service life of the motor 1A in a situation in which the rotational speed thereof is changed.

In addition, a remaining service life of the motor (1A) may be $(1-L_s)$.

A motor control system (MC) according to this embodiment includes a motor (1A) that is driven by variable duty cycle control, and a control unit (3) that reads driving information of the motor (1A). The control unit (3) includes a calculation unit (3A) that calculates an elapsed service life ratio representing a ratio of an elapsed service life to all service life of the motor (1A) according to the following formula:

$$L_s = \sum_i \left(\frac{t_i}{L_i \times (1.5)^m}\right) \quad m = \frac{40 - \max(40, K_i)}{10},$$

where $L_s$ represents the elapsed service life ratio, $t_i$ represents a driving time in a section i, $L_i$ represents a service life expectancy at a duty cycle $D_i$ in the section i and at an environmental temperature of the motor being 40° C., and $K_i$ represents a temperature in the section i.

With the above configuration, it is possible to accurately estimate the service life of the motor 1A in a situation in which the rotational speed thereof is changed.

In addition, the control unit (3) may further include a signal output unit (3C) that outputs an alarm signal when the elapsed service life ratio calculated by the calculation unit (3A) is higher than or equal to a set value.

Thus, it is possible to inform a user that the remaining service life of the motor 1A is low.

In addition, a blower system (5, 51, 52) according to this embodiment includes the motor control system (MC) having the above configuration, and a blower (1) including the motor (1A) and an impeller (1B) that is fixed on a rotation unit of the motor (1A) and that includes a plurality of blades.

Thus, it is possible to accurately estimate the service life of the motor 1A of the blower 1 that performs cooling control by changing the rotational speed of the motor 1A.

In addition, in the blower system (5, 51, 52) having the above configuration, the temperature $K_i$ may be any one of a temperature of an external apparatus (6) that is cooled by the blower (1), an ambient temperature of the external apparatus (6), and an environmental temperature of the motor (1A).

Thus, if the temperature $K_i$ is either the temperature of the CPU 6 that is cooled by the blower 1 or the ambient temperature of the CPU 6, a temperature sensor can be used for both cooling control and the estimation of the service life. In addition, if the temperature $K_i$ is the environmental temperature of the motor 1A, it is possible to estimate the service life with higher accuracy.

In addition, in the blower system (5, 51, 52) having the above configuration, the control unit (3) included in the motor control system (MC) may increase or decrease a rotational speed of the motor (1A) when the temperature of an external apparatus (6) that is cooled by the blower (1) is increased or decreased.

Thus, it is possible to accurately estimate the service life of the motor 1A in a situation in which the rotational speed of the motor 1A is changed in accordance with the temperature of the CPU 6 that is cooled.

Next, an example of a case in which the present disclosure is applied to a multi-copter system will be described.

Figure 7:
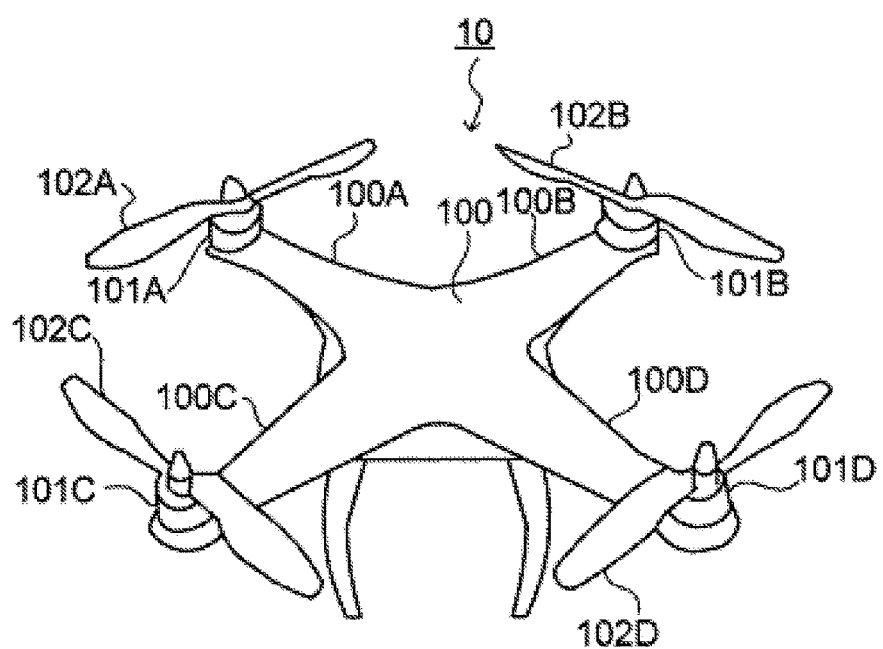
FIG. 7 illustrates a schematic perspective view of the appearance of a multi-copter main body according to a second embodiment of the present disclosure.

FIG. 7 illustrates a schematic perspective view of the appearance of a multi-copter main body 10 according to a second embodiment. The multi-copter main body 10 includes a main body part 100, a first motor 101A, a second motor 101B, a third motor 101C, a fourth motor 101D, a first propeller 102A, a second propeller 102B, a third propeller 102C, and a fourth propeller 102D.

The main body part 100 has a shape that branches from the center in four directions and arms 100A to 100D. The arms 100A to 100D respectively have the first motor 101A, the second motor 101B, the third motor 101C, and the fourth motor 101D at the respective leading ends. The first motor 101A to the fourth motor 101D respectively include motors on which the first propeller 102A to the fourth propeller 102D are fixed. That is, in the multi-copter main body 10, four propellers are rotated by four motors. Note that the number of the motors and the propellers is not limited to four and may be any number larger than 1.

Figure 8:
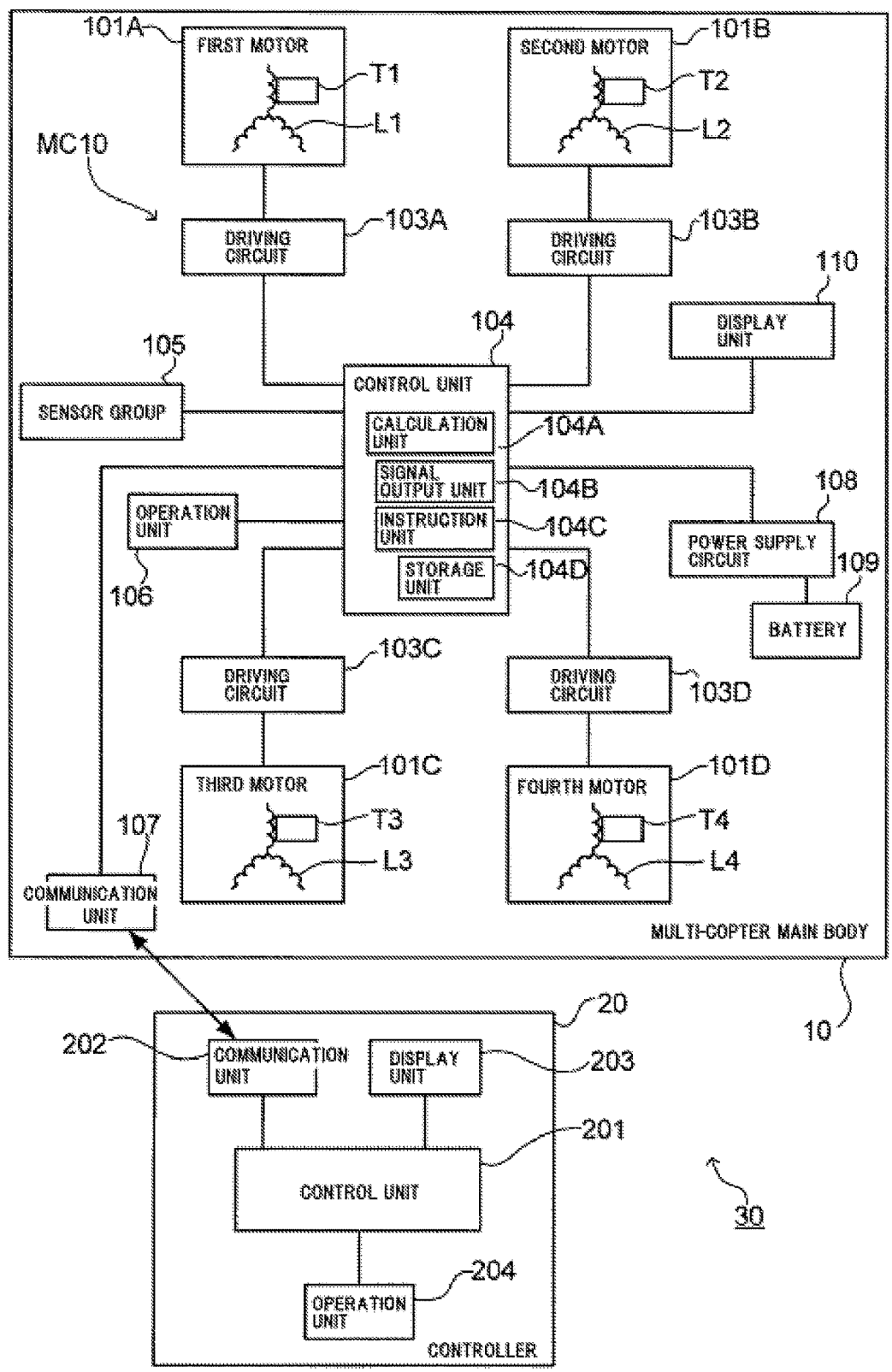
FIG. 8 illustrates a block configuration of a multi-copter system according to the second embodiment of the present disclosure.

FIG. 8 illustrates a block configuration of a multi-copter system 30 according to the second embodiment. As illustrated in FIG. 8, the multi-copter system 30 includes the multi-copter main body 10 and a controller 20.

The multi-copter main body 10 includes the first motor 101A to the fourth motor 101D, driving circuits 103A to 103D, a control unit 104, a sensor group 105, an operation unit 106, a communication unit 107, a power supply circuit 108, a battery 109, and a display unit 110.

The first motor 101A to the fourth motor 101D are configured by brushless DC motors and respectively include coils L1 to L4. The first motor 101A to the fourth motor 101D respectively further include temperature sensors T1 to T4. The temperature sensors T1 to T4 respectively detect the coil temperatures of the coils L1 to L4. As a method for detecting the coil temperatures, for example, a temperature measurement method using a resistance method is employed.

The driving circuits 103A to 103D that respectively drive the first motor 101A to the fourth motor 101D each include a PWM signal generating unit, a driver, and the like.

The control unit 104 is a unit that generally controls the multi-copter main body 10 and is configured by, for example, a microprocessor. The control unit 104 includes a calculation unit 104A, a signal output unit 104B, an instruction unit 104C, and a storage unit 104D, which will be described later.

The sensor group 105 includes, for example, a three-axis gyroscope, a three-axis acceleration sensor, a pneumatic sensor, a magnetic sensor, an ultrasonic sensor, and the like.

The three-axis gyroscope detects the inclination of the multi-copter main body 10 in the longitudinal direction, the inclination thereof in the lateral direction, and the rotational angular velocity thereof, and detects the posture and movement of the multi-copter. The three-axis acceleration sensor detects the acceleration of the multi-copter main body 10 in the longitudinal direction, the lateral direction, and the vertical direction. The pneumatic sensor is used for acquiring the altitude of the multi-copter. The magnetic sensor detects the cardinal points. The ultrasonic sensor transmits ultrasonic waves toward the ground and detects reflected signals, thereby detecting the distance to the ground.

The operation unit 106 includes, for example, hard keys (including power button) for operating the multi-copter main body 10. The communication unit 107 performs wireless communication with the controller 20, which will be described later. For example, Wi-Fi communication is used for the wireless communication.

The power supply circuit 108 is a circuit that supplies electric power to each unit of the multi-copter main body 10 by using electric power supplied from the battery 109. As the battery 109, for example, a lithium polymer secondary battery is used. The display unit 110 is configured by, for example, a liquid crystal display unit, a light-emitting diode (LED) display unit, or the like.

The controller 20 that is used for operating the multi-copter main body 10 includes a control unit 201, a communication unit 202, a display unit 203, and an operation unit 204.

The control unit 201 is a unit that generally controls each unit of the controller 20 and is configured by, for example, a microprocessor. The communication unit 202 performs wireless communication with the communication unit 107 of the multi-copter main body 10. The display unit 203 is configured by, for example, a liquid crystal display unit, an LED display unit, or the like. The operation unit 204 includes, for example, a stick for operating the multi-copter main body 10.

In the multi-copter system 30 having the above configuration, a user holds the controller 20 in hands and operates the multi-copter main body 10 by using the operation unit 204. The operation of the multi-copter includes, for example, rising, falling, rotating, moving forward and backward, and moving right and left. In response to the user's operation by using the operation unit 204, the control unit 201 wirelessly transmits operation signals to the communication unit 107 of the multi-copter main body 10 through the communication unit 202.

The operation signals received by the communication unit 107 are transmitted to the control unit 104. On the basis of the received operation signals, the control unit 104 outputs motor control signals to the driving circuits 103A to 103D. On the basis of the respective motor control signals that have been received, the driving circuits 103A to 103D respectively output driving current to the first motor 101A to the fourth motor 101D to control the driving of the respective motors. Specifically, the driving circuits 103A to 103D control the rotational speeds of the motors by variable duty cycle control, thereby operating the multi-copter of the multi-copter main body 10. Note that the driving circuits 103A to 103D can detect the rotational speeds of the motors on the basis of current signals or voltage signals generated in the first motor 101A to the fourth motor 101D.

The control unit 104 continuously receives detection signals from the sensor group 105 and outputs, on the basis of the acquired detection signals, motor control signals that are appropriate for the driving circuits 103A to 103D.

The control unit 104 can estimate the service life of each of the first motor 101A to the fourth motor 101D. Specifically, the calculation unit 104A included in the control unit 104 calculates an elapsed service life ratio according to the following Formula (3):

$$L_s = \sum_i \left( \frac{t_i}{L_i \times (1.5)^m} \right) \quad m = \frac{(40 + \Delta t) - \max(40 + \Delta t, K_i)}{10}, \quad (3)$$

where $L_s$ represents the elapsed service life ratio, $t_i$ represents a driving time in a section i, $L_i$ represents a service life expectancy at a duty cycle $D_i$ in the section i and at an environmental temperature of the motor being 40° C., $K_i$ represents a temperature of the motor in the section i, and $\Delta t$ represents a temperature increase value of the motor at the duty cycle $D_i$ in the section i and at the environmental temperature of the motor being 40° C.

The storage unit 104D included in the control unit 104 stores in advance, for example, a table representing the relationship among the duty cycle, the service life expectancy, and the temperature increase value $\Delta t$ as illustrated in FIG. 2 described above. The service life expectancy corresponding to the duty cycle $D_i$ in the table is used as $L_i$ in the above Formula (3). The temperature increase value corresponding to the duty cycle $D_i$ in the table is used as $\Delta t$ in the above Formula (3). The calculation unit 104A reads information about the duty cycle from the driving circuits 103A to 103D.

In addition, each of the coil temperatures detected by the temperature sensors T1 to T4 is used as $K_i$ in the above Formula (3). In the multi-copter main body 10, the temperature of a motor may be increased by an external cause due to a component such as a battery or a circuit substrate or environment such as sunlight or humidity. Accordingly, in this embodiment, the temperatures of the first motor 101A to the fourth motor 101D are detected by the temperature sensors T1 to T4 to be used for calculation according to the above Formula (3). Note that the temperature sensors may each detect, for example, the temperature of the internal space of a housing of the corresponding motor in addition to the coil temperature.

The rotational speeds of the first motor 101A to the fourth motor 101D are controlled to be changed in order to control the multi-copter main body 10. However, since a change in the duty cycle corresponds to a change in the rotational speed, the calculation of the elapsed service life ratio according to the above Formula (3) enables accurate estimation of the service life of each of the first motor 101A to the fourth motor 101D.

The multi-copter system 30 according to this embodiment has a function of detecting a low remaining service life of a motor and informing a user of an alarm. Now, this function will be described with reference to the flowcharts in FIG. 9 and FIG. 10.

In this case, the calculation unit 104A included in the control unit 104 calculates the elapsed service life ratio of each of the first motor 101A to the fourth motor 101D. The calculated elapsed service life ratio is stored in the storage unit 104D included in the control unit 104.

Figure 9:
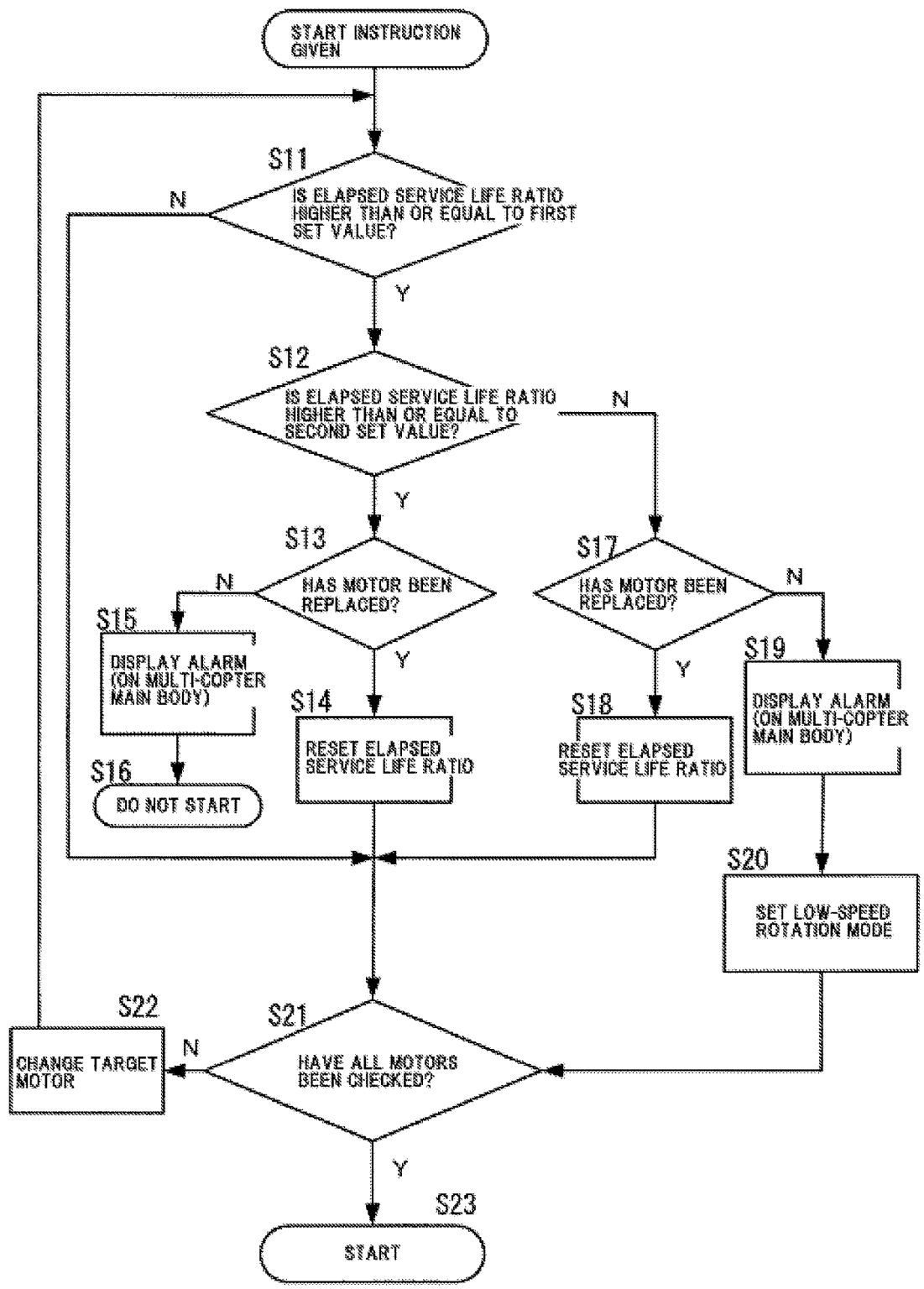
FIG. 9 is a flowchart illustrating a process performed when a multi-copter according to the second embodiment of the present disclosure is started.

For example, when a start instruction is given by an operation (e.g., switching on power button) by using the operation unit 106 of the multi-copter main body 10, the flowchart in FIG. 9 starts. First, in step S11 in FIG. 9, the control unit 104 checks the elapsed service life ratio of a target motor among the elapsed service life ratios of the first motor 101A to the fourth motor 101D stored in the storage unit 104D, and determines whether the elapsed service life ratio of the target motor is higher than or equal to a first set value. The first set value is set to, for example, 0.8. If the elapsed service life ratio is not higher than or equal to the first set value (N in step S11), the process proceeds to step S21.

In step S21, it is determined whether the control unit 104 has checked the elapsed service life ratios of all the motors. If the checking is not performed yet (N in step S21), the control unit 104 changes the target motor (step S22), and the process returns to step S11.

If the elapsed service life ratio is higher than or equal to the first set value in step S11 (Y in step S11), the process proceeds to step S12 in which the control unit 104 determines whether the elapsed service life ratio is higher than or equal to a second set value that is higher than the first set value. The second set value is set to, for example, 0.9. If the elapsed service life ratio is not higher than or equal to the second set value (N in step S12), it is determined that the remaining service life of the target motor is low, and the process proceeds to step S17.

In step S17, the control unit 104 determines whether the target motor has been replaced by a new motor. The determination as to whether the motor has been replaced can be performed by, for example, reading an ID or the like stored in the motor and determining whether the ID or the like has been changed.

If the motor has not been replaced (N in step S17), the process proceeds to step S19, and the signal output unit 104B included in the control unit 104 outputs a display control signal as an alarm signal to the display unit 110. Thus, the display unit 110 performs a display operation to encourage a user to replace the target motor. If the display unit 110 is, for example, a liquid crystal display unit, the display unit 110 may display characters or the like to encourage a user to replace the motor. If the display unit 110 is, for example, an LED display unit, the display unit 110 may turn on a corresponding LED to encourage, by using the color of the light, a user to replace the motor. Note that the signal output unit 104B may transmit a display control signal to the controller 20 through the communication unit 107 so as to cause the display unit 203 of the controller 20 to perform an alarm display operation.

After step S19, the process proceeds to step S20 in which the control unit 104 sets a low-speed rotation mode in which the first motor 101A to the fourth motor 101D are rotated at a low speed, and then the process proceeds to step S21.

On the other hand, if it is determined in step S17 that the target motor has been replaced by a new motor (Y in step S17), the process proceeds to step S18 in which the control unit 104 resets the target elapsed service life ratio to zero. After step S18, the process proceeds to step S21.

If the elapsed service life ratio is higher than or equal to the second set value in step S12 (Y in step S12), it is determined that the remaining service life of the target motor is extremely low, and the process proceeds to step S13. In step S13, the control unit 104 determines whether the target motor has been replaced by a new motor. If the target motor has not been replaced (N in step S13), the process proceeds to step S15 in which the signal output unit 104B outputs a display control signal as an alarm signal to the display unit 110. Thus, the display unit 110 performs a display operation to encourage a user to replace the target motor. The display operation here may be a display operation by which a user is informed that the target motor needs to be replaced immediately compared with the display operation in step S19.

Subsequently, the process proceeds to step S16 in which the control unit 104 controls the power supply circuit 108 so as at least not to supply power to the driving circuits 103A to 103D. That is, power application to the first motor 101A to the fourth motor 101D is stopped, and the multi-copter main body 10 is not started.

On the other hand, if it is determined in step S13 that the motor has been replaced (Y in step S13), the process proceeds to step S14 in which the control unit 104 resets the target elapsed service life ratio to zero. After step S14, the process proceeds to step S21.

If it is determined in step S21 that the elapsed service life ratios of all of the first motor 101A to the fourth motor 101D have been checked (Y in step S21), the process proceeds to step S23. In step S23, the control unit 104 controls the power supply circuit 108 so as to supply power to units including the driving circuits 103A to 103D, thereby enabling power to be applied to the first motor 101A to the fourth motor 101D. That is, the multi-copter main body 10 is started. Subsequently, by operating the controller 20, a user can control the flight of the multi-copter main body 10.

If the low-speed rotation mode has already been set in step S20, subsequently, the instruction unit 104C included in the control unit 104 transmits, to the driving circuits 103A to 103D, motor control signals by which the first motor 101A to the fourth motor 101D are driven with the rotational speeds thereof restricted. That is, the instruction unit 104C gives an instruction for driving the motors in the low-speed rotation mode.

Figure 10:
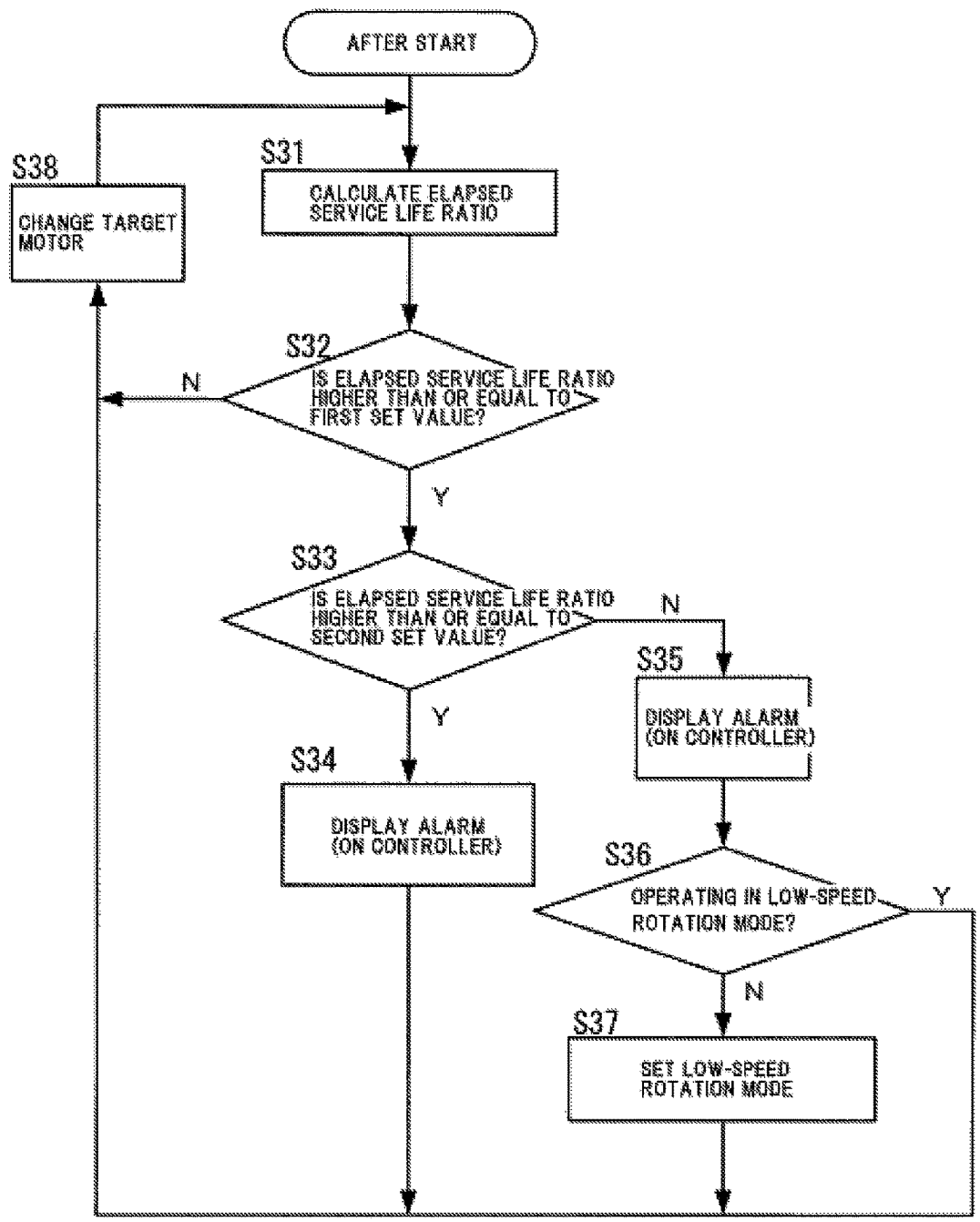
FIG. 10 is a flowchart illustrating a process performed after the multi-copter according to the second embodiment of the present disclosure has been started.

When the multi-copter main body 10 is started in step S23, the process proceeds to the flowchart in FIG. 10. In FIG. 10, first, in step S31, the calculation unit 104A included in the control unit 104 calculates the elapsed service life ratio of a target motor among the first motor 101A to the fourth motor 101D.

Subsequently, the process proceeds to step S32 in which the control unit 104 determines whether the calculated elapsed service life ratio is higher than or equal to the first set value. If the elapsed service life ratio is not higher than or equal to the first set value (N in step S32), the process proceeds to step S38 in which the target motor is changed, and then the process returns to step S31.

On the other hand, if the elapsed service life ratio is higher than or equal to the first set value (Y in step S32), the process proceeds to step S33 in which the control unit 104 determines whether the elapsed service life ratio is higher than or equal to the second set value. If the elapsed service life ratio is not higher than or equal to the second set value (N in step S33), the process proceeds to step S35.

In step S35, the signal output unit 104B included in the control unit 104 outputs a display control signal as an alarm signal to the communication unit 107. Thus, the display control signal is transmitted from the communication unit 107 to the controller 20, and on the basis of the display control signal, the display unit 203 in the controller 20 performs a display operation to encourage a user to replace the target motor. Thus, a user can be informed of an alarm from the controller 20 in their hands while the multi-copter main body 10 is flying.

Subsequently, the process proceeds to step S36, the control unit 104 determines whether the low-speed rotation mode has already been set. If the low-speed rotation mode has already been set (Y in step S36), the process proceeds to step S38. On the other hand, if the low-speed rotation mode has not been set (N in step S36), the process proceeds to step S37 in which the control unit 104 sets the low-speed rotation mode. Subsequently, the instruction unit 104C gives an instruction for driving the motors in the low-speed rotation mode. After step S37, the process proceeds to step S38.

If it is determined in step S33 that the elapsed service life ratio is higher than or equal to the second set value (Y in step S33), the process proceeds to step S34 in which the signal output unit 104B included in the control unit 104 outputs a display control signal as an alarm signal to the communication unit 107. Thus, the display control signal is transmitted from the communication unit 107 to the controller 20, and on the basis of the display control signal, the display unit 203 in the controller 20 performs a display operation to encourage a user to replace the target motor. The display operation here may be a display operation for indicating that the target motor needs to be replaced immediately compared with the display operation in step S35. Subsequently, the process proceeds to step S38.

The process illustrated in FIG. 10 is continued by repeatedly changing the target motor in step S38, while the multi-copter main body 10 is operated. Note that the elapsed service life ratio that has been calculated and stored in the storage unit 104D is used for the determination in the process for starting the multi-copter main body 10 in FIG. 9.

Through the above processes, a user is informed of an alarm before the end of the service life of the motor and thus can be encouraged to replace the motor. Thus, a multi-copter system with high safety can be realized.

Thus, a method for estimating a service life of a motor according to this embodiment is a method for estimating a service life of a motor (101A to 101D) that is driven by variable duty cycle control, the method including calculating an elapsed service life ratio representing a ratio of an elapsed service life to all service life according to the following formula to estimate the service life of the motor:

$$L_s = \sum_i \left( \frac{t_i}{L_i \times (1.5)^m} \right) \quad m = \frac{(40 + \Delta t) - \max(40 + \Delta t, K_i)}{10},$$

where $L_s$ represents the elapsed service life ratio, $t_i$ represents a driving time in a section i, $L_i$ represents a service life expectancy at a duty cycle $D_i$ in the section i and at an environmental temperature of the motor being 40° C., $K_i$ represents a temperature of the motor in the section i, and $\Delta t$ represents a temperature increase value of the motor at the duty cycle $D_i$ in the section i and at the environmental temperature of the motor being 40° C.

With the above configuration, it is possible to accurately estimate the service life of each of the first motor 101A to the fourth motor 101D in a situation in which the rotational speeds thereof are changed.

In addition, according to this embodiment, a motor control system MC10 is configured by the control unit 104, the driving circuits 103A to 103D, and the first motor 101A to the fourth motor 101D in the multi-copter main body 10 (FIG. 8).

A motor control system (MC10) includes a motor (101A to 101D) that is driven by variable duty cycle control, and a control unit (104) that reads driving information of the motor. The control unit (104) includes a calculation unit (104A) that calculates an elapsed service life ratio representing a ratio of an elapsed service life to all service life of the motor according to the following formula:

$$L_s = \sum_i \left( \frac{t_i}{L_i \times (1.5)^m} \right) \quad m = \frac{(40 + \Delta t) - \max(40 + \Delta t, K_i)}{10},$$

where $L_s$ represents the elapsed service life ratio, $t_i$ represents a driving time in a section i, $L_i$ represents a service life expectancy at a duty cycle $D_i$ in the section i and at an environmental temperature of the motor being 40° C., $K_i$ represents a temperature of the motor in the section i, and $\Delta t$ represents a temperature increase value of the motor at the duty cycle $D_i$ in the section i and at the environmental temperature of the motor being 40° C.

In addition, a multi-copter system (30) according to this embodiment includes the motor control system (MC10) having the above configuration, a multi-copter main body (10) including the motor (101A to 101D) and a propeller (102A to 102D) that is rotatable by the motor.

Thus, in a system that controls the flight of the multi-copter main body 10 by changing the rotational speeds of the motors 101A to 101D, it is possible to accurately estimate the service life of the motors. Accordingly, a multi-copter system with high safety can be realized.

Note that in the second embodiment, the controller 20 may also include a control unit having substantially the same functions as the control unit 104. In this case, a calculation unit included in the control unit included in the controller 20 acquires information about the duty ratio and information about the temperature from the multi-copter main body 10 by using wireless communication, thereby calculating the elapsed service life ratio.

The present disclosure is applicable as appropriate to a motor included in a variety of apparatuses such as a blower and a multi-copter.

Features of the above-described preferred embodiments and the modifications thereof may be combined appropriately as long as no conflict arises.

While preferred embodiments of the present invention have been described above, it is to be understood that variations and modifications will be apparent to those skilled in the art without departing from the scope and spirit of the present invention. The scope of the present invention, therefore, is to be determined solely by the following claims.

What is claimed is:

1. A method for estimating a service life of a motor that is driven by variable duty cycle control, the method comprising:

reading information about a duty cycle from a driving circuit and acquiring information about a temperature which is detected by a temperature sensor;

determining whether the duty cycle has changed from a last-time duty cycle;

determining whether the temperature has changed from a last-time temperature;

calculating an elapsed service life ratio representing a ratio of an elapsed service life to all service life according to the following formula to estimate the service life of the motor:

$$L_s = \sum_i \left( \frac{t_i}{L_i \times (1.5)^m} \right) \quad m = \frac{40 - \max(40, K_i)}{10},$$

wherein $L_s$ represents the elapsed service life ratio, $t_i$ represents a driving time in a section i, the section i being a temporal section used in the calculating and which corresponds to the last-time duty cycle, the last-time temperature, and a currently counted driving time, $L_i$ represents a service life expectancy at a duty cycle $D_i$ in the section i and at an environmental temperature of the motor being 40° C., and $K_i$ represents a temperature in the section i; and outputting a signal which relates to the calculated elapsed service life ratio calculated by the calculating.

2. The method for estimating the service life of the motor according to claim 1, wherein a remaining service life of the motor is $(1-L_s)$.

3. A motor control system comprising:

a motor that is driven by variable duty cycle control; and control circuit that reads driving information of the motor, reads information about a duty cycle from a driving circuit, and acquires information about a temperature which is detected by a temperature sensor; wherein the control circuitry determines whether the duty cycle has changed from a last-time duty cycle and determines whether the temperature has changed from a last-time temperature;

the control circuitry includes calculation circuitry that calculates an elapsed service life ratio representing a ratio of an elapsed service life to all service life of the motor according to the following formula:

$$L_s = \sum_i \left(\frac{t_i}{L_i \times (1.5)^m}\right) \quad m = \frac{40 - \max(40, K_i)}{10},$$

wherein $L_s$ represents the elapsed service life ratio, $t_i$ represents a driving time in a section i, the section i being a temporal section used in calculation by the calculation circuitry and which corresponds to the last-time duty cycle, the last-time temperature, and a currently counted driving time, $L_i$ represents a service life expectancy at a duty cycle $D_i$ in the section i and at an environmental temperature of the motor being 40° C., and $K_i$ represents a temperature in the section i; and the control circuitry outputs a signal which relates to the calculated elapsed service life ratio calculated by the calculation circuitry.

4. The motor control system according to claim 3, wherein the control circuitry further includes signal output circuitry that outputs an alarm signal when the elapsed service life ratio calculated by the calculation circuitry is higher than or equal to a set value.

5. A blower system comprising:

the motor control system according to claim 3; and a blower including the motor, and an impeller that is fixed on a rotating assembly of the motor and that includes a plurality of blades.

6. The blower system according to claim 5, wherein the temperature is any one of a temperature of an external apparatus that is cooled by the blower, an ambient temperature of the external apparatus, and an environmental temperature of the motor.

7. The blower system according to claim 5, wherein the control circuitry included in the motor control system increases or decreases a rotational speed of the motor when the temperature of an external apparatus that is cooled by the blower is increased or decreased.

8. A method for estimating a service life of a motor that is driven by variable duty cycle control, the method comprising:

reading information about a duty cycle from a driving circuit and acquiring information about a temperature which is detected by a temperature sensor;

determining whether the duty cycle has changed from a last-time duty cycle;

determining whether the temperature has changed from a last-time temperature;

calculating an elapsed service life ratio representing a ratio of an elapsed service life to all service life according to the following formula to estimate the service life of the motor:

$$L_s = \sum_i \left(\frac{t_i}{L_i \times (1.5)^m}\right) \quad m = \frac{(40 + \Delta t) - \max(40 + \Delta t, K_i)}{10},$$

wherein $L_s$ represents the elapsed service life ratio, $t_i$ represents a driving time in a section i, the section i being a temporal section used in the calculating which corresponds to the last-time duty cycle, the last-time temperature, and a currently counted driving time, $L_i$ represents a service life expectancy at a duty cycle $D_i$ in the section i and at an environmental temperature of the motor being 40° C., $K_i$ represents a temperature of the motor in the section i, and $\Delta t$ represents a temperature increase value of the motor at the duty cycle $D_i$ in the section i and at the environmental temperature of the motor being 40° C.; and outputting a signal which relates to the calculated elapsed service life ratio calculated by the calculating.

9. A motor control system comprising:

a motor that is driven by variable duty cycle control; and control circuitry that reads driving information of the motor, reads information about a duty cycle from a driving circuit, and acquires information about a temperature which is detected by a temperature sensor; wherein the control circuitry determines whether the duty cycle has changed from a last-time duty cycle and determines whether the temperature has changed from a last-time temperature;

the control circuitry includes calculation circuitry that calculates an elapsed service life ratio representing a ratio of an elapsed service life to all service life of the motor according to the following formula:

$$L_s = \sum_i \left(\frac{t_i}{L_i \times (1.5)^m}\right) \quad m = \frac{(40 + \Delta t) - \max(40 + \Delta t, K_i)}{10},$$

wherein $L_s$ represents the elapsed service life ratio, $t_i$ represents a driving time in a section i, the section i being a temporal section used in calculation by the calculation circuitry and which corresponds to the last-time duty cycle, the last-time temperature, and a currently counted driving time, $L_i$ represents a service life expectancy at a duty cycle $D_i$ in the section i and at an environmental temperature of the motor being 40° C., $K_i$ represents a temperature of the motor in the section i, and Δt represents a temperature increase value of the motor at the duty cycle $D_i$ in the section i and at the environmental temperature of the motor being 40° C.; and the control circuitry outputs a signal which relates to the calculated elapsed service life ratio calculated by the calculation circuitry.

10. A multi-copter system comprising:
the motor control system according to claim 9; and
a multi-copter main body including
    the motor, and
    a propeller that is rotatable by the motor.

* * * * *